(12) United States Patent
Alleyne et al.

(10) Patent No.: US 7,407,513 B2
(45) Date of Patent: Aug. 5, 2008

(54) ARTIFICIAL SPINAL DISK

(75) Inventors: Neville Alleyne, La Jolla, CA (US);
James R. Gerchow, Sturgis, MI (US);
Makoto Nonaka, La Jolla, CA (US);
Philip James Sluder, El Cajon, CA (US)

(73) Assignee: Smart Disc, Inc., Allen Park, MI (US)

( * ) Notice: Subject to any disclaimer, the term of this patent is extended or adjusted under 35 U.S.C. 154(b) by 447 days.

(21) Appl. No.: 10/838,515

(22) Filed: May 3, 2004

(65) Prior Publication Data

US 2005/0107881 A1 May 19, 2005

Related U.S. Application Data

(60) Provisional application No. 60/513,238, filed on Oct. 21, 2003, provisional application No. 60/467,655, filed on May 2, 2003.

(51) Int. Cl.
*A61F 2/44* (2006.01)

(52) U.S. Cl. .................. 623/17.16; 623/17.15; 606/246

(58) Field of Classification Search .............. 623/17.11, 623/17.12, 17.13, 17.14, 17.15, 17.16; 606/246
See application file for complete search history.

(56) References Cited

U.S. PATENT DOCUMENTS

| 5,895,428 | A | 4/1999 | Berry | |
|---|---|---|---|---|
| 6,572,653 | B1 | 6/2003 | Simonson | |
| 2002/0035400 | A1* | 3/2002 | Bryan et al. | 623/17.15 |
| 2002/0099444 | A1* | 7/2002 | Boyd et al. | 623/17.16 |
| 2003/0069639 | A1* | 4/2003 | Sander et al. | 623/17.11 |
| 2004/0117021 | A1* | 6/2004 | Biedermann et al. | 623/17.15 |
| 2004/0236425 | A1* | 11/2004 | Huang | 623/17.12 |

FOREIGN PATENT DOCUMENTS

| DE | 239 523 A | 10/1986 |
|---|---|---|
| DE | 90 00 094 U | 1/1991 |
| EP | 0 809 986 A | 12/1997 |

\* cited by examiner

*Primary Examiner*—Corrine McDermott
*Assistant Examiner*—Javier G Blanco
(74) *Attorney, Agent, or Firm*—Knobbe Martens Olson & Bear LLP

(57) ABSTRACT

An artificial spinal disk comprises a central capsule that is configured to slide laterally within the disk space with one or more of flexion, extension, and lateral bending of the spine so as to shift an instantaneous center of rotation of the artificial disk. In one embodiment, the invention comprises an artificial spinal disk comprising a first plate having an inwardly directed surface, a second plate having an inwardly directed surface facing generally toward the inwardly directed surface of the first plate, and a central capsule with outwardly directed opposed faces that slidably mate with the inwardly directed surfaces of the first and second plates.

6 Claims, 12 Drawing Sheets

ARTIFICIAL SPINAL DISK

CROSS REFERENCE TO RELATED APPLICATIONS

This application claims priority under 35 U.S.C. Section 119(e) to U.S. Provisional Applications 60/467,655 filed on May 2, 2003 and 60/513,238 filed Oct. 21, 2003. The disclosures of both of these applications are hereby incorporated by reference in their entireties.

BACKGROUND OF THE INVENTION

A wide variety of artificial spinal disk designs have been developed over the past several years. Some designs, such as those described in U.S. Pat. Nos. 6,001,130 and 5,123,926 include resilient plastic or fluid filled bag type structures that are placed between adjacent vertebra. These designs provide flexibility, but present the risk of rupture or breakage, and can be difficult to contain effectively within the disk space. Other designs have attempted to use ball-and socket type couplers between endplates or other retaining devices attached to the vertebral bodies. Currently, devices which use metal-metal interfaces rather than resilient bodies are favored for their reliability and strength. However, these types of couplings do a poor job of imitating the natural relative movement of vertebral bodies separated by a natural anatomical disk. Furthermore, this type of replacement disk typically focuses all the forces from weight and motion in a single direction and on a very small part of each vertebral body. This can cause excessive stress on the bone in the area where the artificial disk connects to the vertebral body. Improved designs that reduce these problems are needed in the art.

SUMMARY OF THE INVENTION

An artificial spinal disk comprises a central capsule that is configured to slide laterally within the disk space with one or more of flexion, extension, and lateral bending of the spine so as to shift an instantaneous center of rotation of the artificial disk. In one embodiment, the invention comprises an artificial spinal disk comprising a first plate having an inwardly directed surface, a second plate having an inwardly directed surface facing generally toward the inwardly directed surface of the first plate, and a. central capsule with outwardly directed opposed faces that slidably mate with the inwardly directed surfaces of the first and second plates.

In another embodiment, an artificial spinal disk comprises a plurality of separate pieces, wherein the separate pieces are configured and sized to be placed in the disk space separate from one another. The pieces comprise couplers such that the separate pieces are attached to form a completed artificial disk only after installation within the disk space. In one such embodiment, the separate pieces of the artificial disk comprise at least first and second bone plates and a central capsule.

Methods of spine surgery are also provided. In one embodiment, a method of spine surgery comprises placing a first portion of an artificial disk into a disk space; and separately placing one or more additional portions of the artificial disk into the disk space and mechanically coupling the additional portions to one or more portions previously placed inside the disk space so as to assemble a complete artificial disk within the disk space from artificial disk pieces that are separate outside of the disk space.

In another embodiment of the invention, a surgical kit for spinal surgery comprises a first bone plate configured for attachment to a first vertebral body;

a second bone plate configured for attachment to a second vertebral body; and a central capsule configured to couple to the first bone plate and the second bone plate;

wherein the first bone plate, the second bone plate, and the central capsule are uncoupled from one another to allow for separate installation in a disk space during spine surgery. In some embodiments, the first bone plate and the second bone plate comprise a plurality of uncoupled segments.

BRIEF DESCRIPTION OF THE DRAWINGS

FIG. 11A, 11B, 11C, 11D, 11E illustrates a three-piece bone plate coupling the sliding capsules to upper and lower vertebral bodies.

DETAILED DESCRIPTION

Figure 1A:
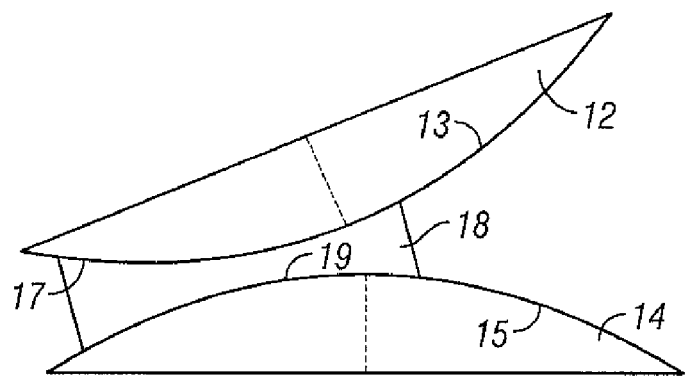
FIGS. 1A, 1B, and 1C are side views of a first emobodiment of an artificial spinal disk with a sliding capsule.
Figure 1B:
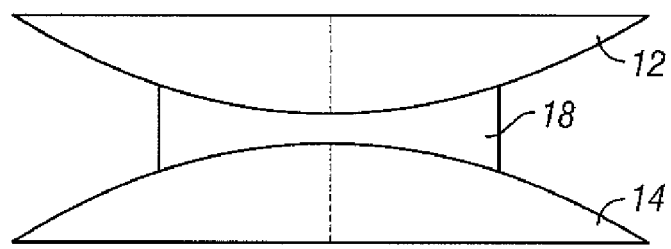
Figure 1C:
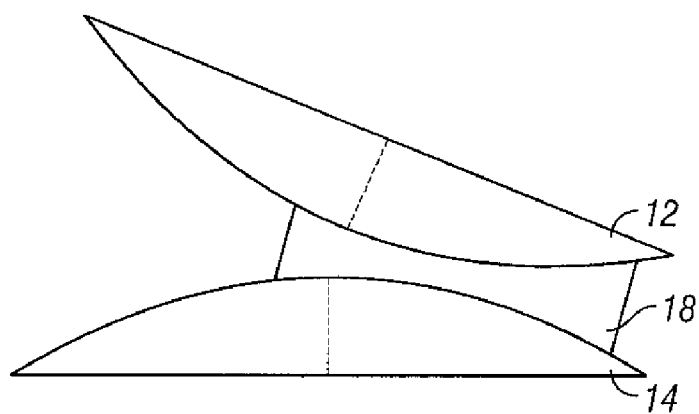

One embodiment of an artificial disk in accordance with the invention is shown in FIGS. 1A, 1B and 1C. In this embodiment, endplates 12, 14 sandwich a sliding central capsule 18. As shown in these Figures, a first plate 12 defines a first inwardly directed surface 13 and the second plate 14 defines a second inwardly directed surface 15. A central capsule 18 defines opposed outwardly directed surfaces 17, 19 that slidably mate with the inwardly directed surfaces of the plates. Thus, the central capsule can slide toward and away from opposed edge portions of the endplates as the relative endplate orientation changes during flexion, extension or lateral bending of the motion segment in which the artificial disk is installed. With this design, the endplates 12, 14 can also rotate with respect to one another as the central capsule slides between them. In this embodiment, the endplates have convex spherical contours, and the central capsule 18 is generally cylindrical with top and bottom surfaces that are concave spherical contours mating with the convex spherical contours on the endplates. Thus, the central capsule 18 is generally cylindrical with a hour-glass shaped cross-section.

Figure 2A:
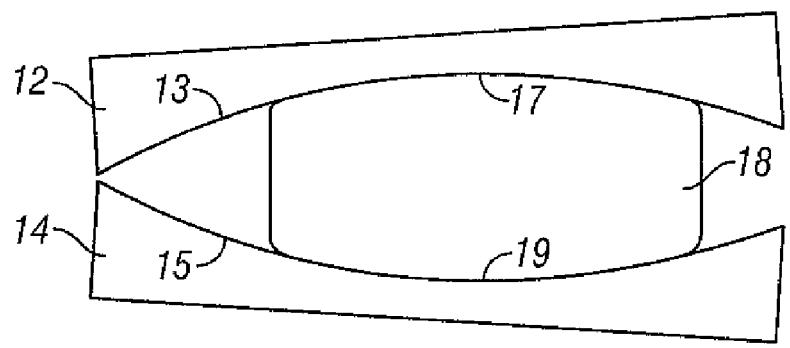
FIGS. 2A, 2B, and 2C are side views of a second embodiment of an artificial spinal disk with a sliding capsule.
Figure 2B:
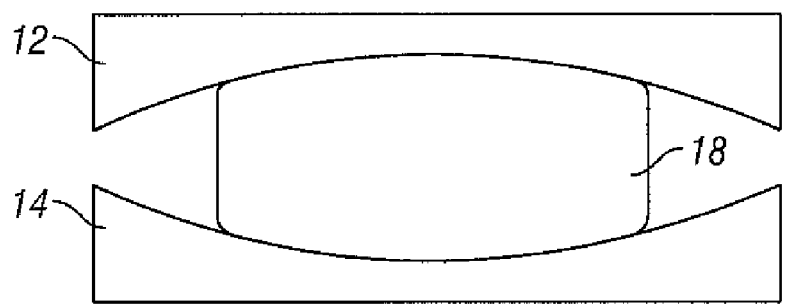
Figure 2C:
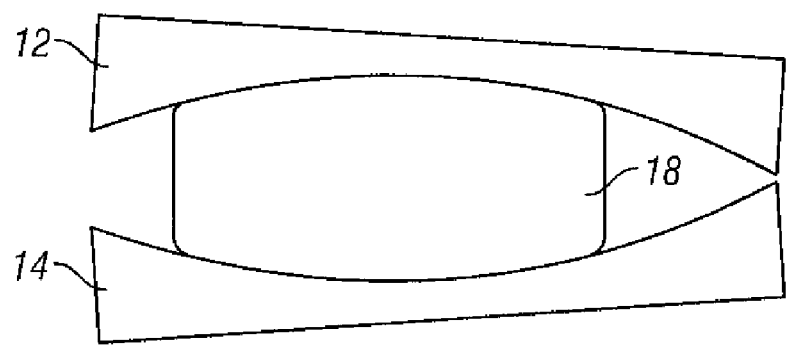

Another embodiment of an artificial disk with a central sliding capsule is illustrated in FIGS. 2A, 2B, and 2C. In this embodiment, the inner surfaces 13, 15 of the endplates 12, 14 are concave rather than convex. The capsule 18 includes mating convex surfaces 17, 19 that slides along the endplate surfaces in a manner analogous to that shown in FIGS. 1A, 1B, and 1C.

There are a variety of important benefits of such a sliding capsule 18. One is that the instantaneous center of rotation of the motion segment is allowed to move around inside the disk space with the capsule during lateral bending, flexion, and extension. Also, the central capsule spreads mechanical stresses over a larger portion of the endplates and thus over the adjacent vertebral bodies as well. This mimics the natural behavior of a spinal disk much better than existing artificial disk designs. Also, this leads to a reduced tendency for migration and loosening following installation, since stresses due to spinal movements are not continually focused in the same direction or location.

Figure 3A:
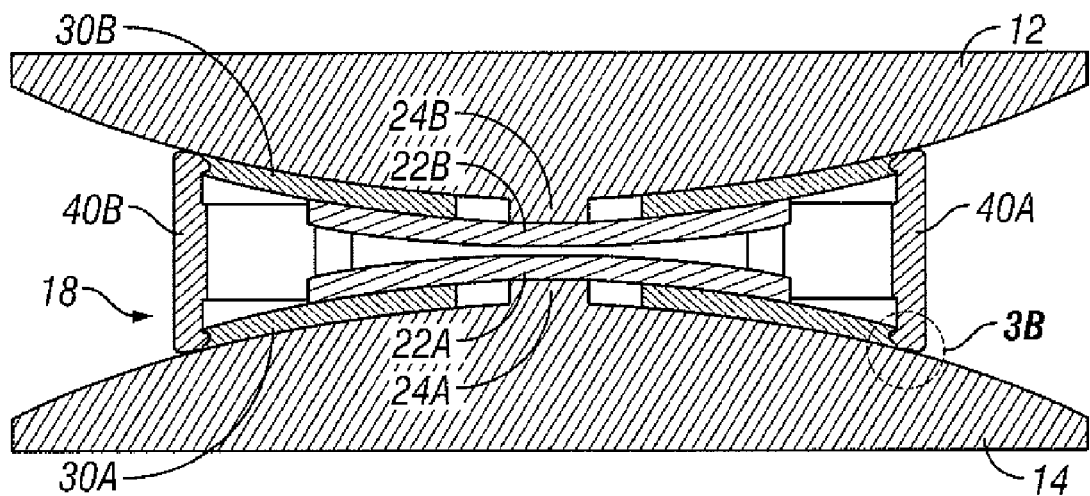
FIGS. 3A and 3B show a cross sectional view of a specific embodiment of the sliding capsule design of FIG. 1.
Figure 3B:
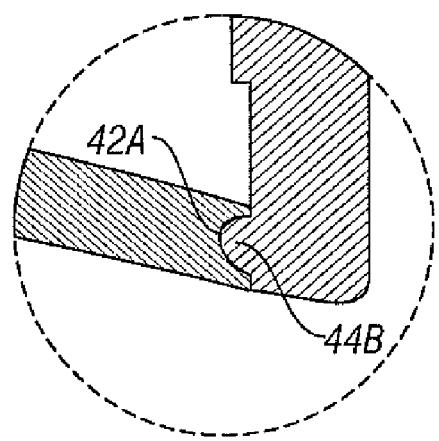
Figure 4:
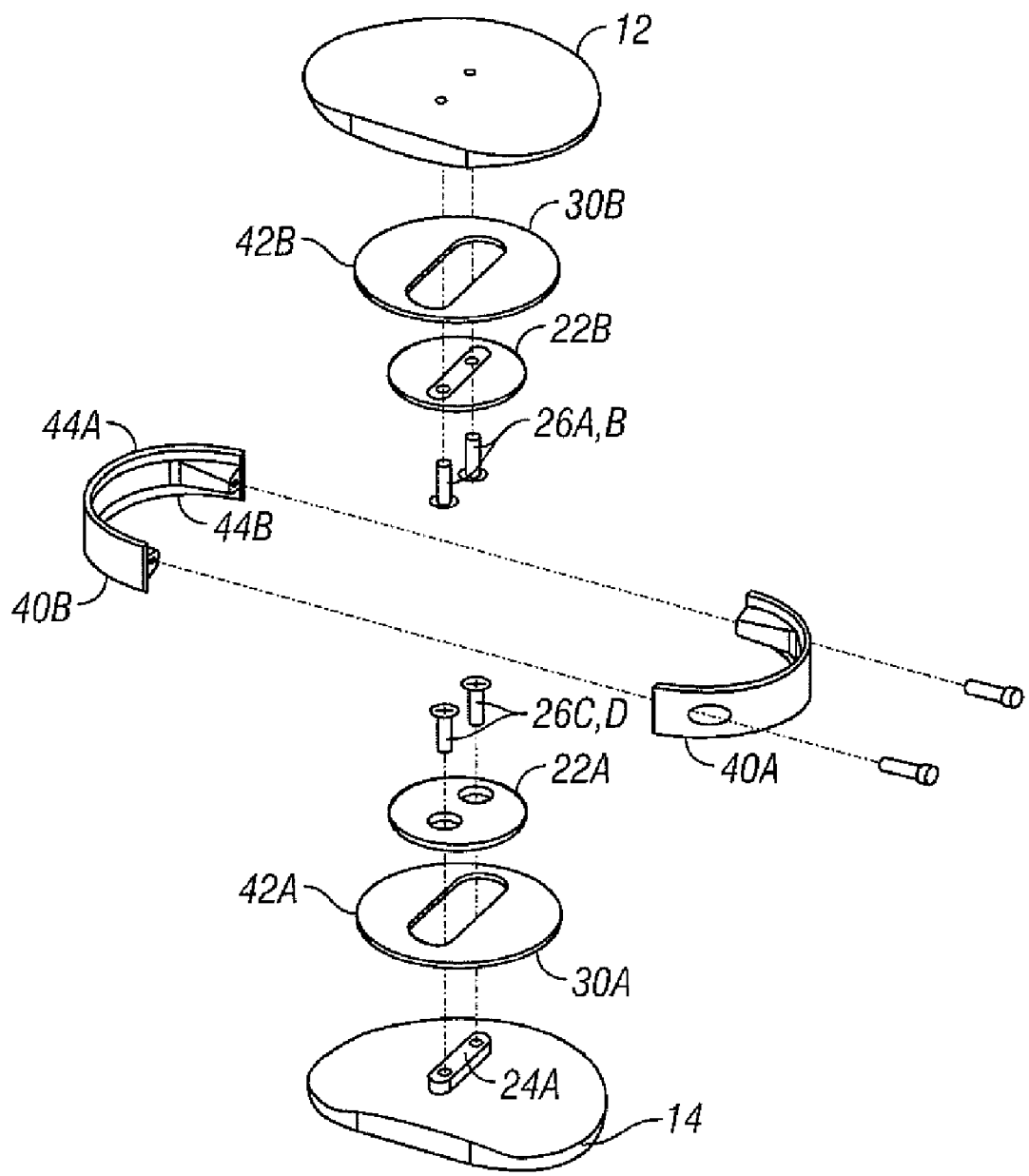
FIG. 4 is an exploded view of the disk of FIG. 3.

One mechanical design for implementing the above described sliding capsule is shown in FIGS. 3 and 4. Referring now to these figures, retainer disks 22A and 22B are secured to respective end plates 14 and 12 on pedestals 24A and 24B with screws (designated 26A, B, C, and D in FIG. 4). The retainer disks also have a spherical contour substantially matching that of the endplates. The pedestals 24A, 24B may be captured in the end plates in recesses or they may be integral with the end plates as shown in FIG. 3. Each retainer disk is secured tightly to the pedestal with the screws such that it does not move with respect to the endplate. Because of the pedestal, however, the underside of each retainer disk is raised up off of the inside spherically contoured surface of the endplate by the height of the pedestal. In an alternative embodiment, a single screws can be used, or a single screw can be made integral with their respective retainer disks 22A, 22B, with the retainer disks held away from the surfaces of the plates without the pedestals by screwing the threaded shafts down to a stop in the plate, for example. If desired, a ring clip or other device could be used to fix unthreaded shafts for the retainer disks 22A, 22B, such that the disks themselves are fixed away from the surfaces of the plates but are allowed to rotate about their central axes.

Captured underneath each endplate, between the surface of the endplate and the underside of each retainer disk, are sliding inner disks 30A and 30B, which are also spherically contoured to match the contour of the endplate inner surfaces. The thickness of these sliding disks 30A, 30B is selected with respect to the height of the pedestals 24A, 24B such that each disk 30A and 30B are slidably captured between the inner surface of the endplate and the underside of the respective retainer disk. The two separate endplates, with attached sliding and retainer disks, are held in facing relation by a sliding inner disk clamp, which in this embodiment comprises two parts, designated 40A and 40B in these Figures, and which are held to each other with screws. The clamp pieces 40A and 40B engage the edges of the sliding disks 30A and 30B in a tongue and groove arrangement. In the pictured embodiment, the edge of each sliding inner disk 30A and 30B is provided with a groove 42A and 42B, and the inner surface of the clamp is provided with a pair of extending flanges 44A and 44B. When the flanges on the clamp engage the grooves of the sliding disks 30A and 30B, a cylindrical sliding assembly with an hourglass shaped cross section is created comprising the clamp 40A, 40B and the sliding disks 30A, 30B. This sliding assembly couples the endplates via the position of the sliding disks under the retainer disks and is slidable with respect thereto between the endplates and the retainer disks 22A and 22B.

The amount of lateral motion and rotation that the sliding assembly is allowed is governed by the shape and size of central openings in the sliding disks with respect to the shape and size of the pedestals 24A and 24B fixed to the center of the endplates. The sliding disks will be able to slide away from the center and rotate until the edges of the openings in the sliding disks contact the sides of the pedestals. In one embodiment, it has been found advantageous for the relative dimensions of these features to allow for a few millimeters of lateral movement. For round pedestals and openings, rotation around the central axis of the device is unlimited throughout 360 degrees. It has been found advantageous, however, to use the oblong shapes shown in FIG. 4, which limit rotation to about 30-60 degrees.

Figure 5A:
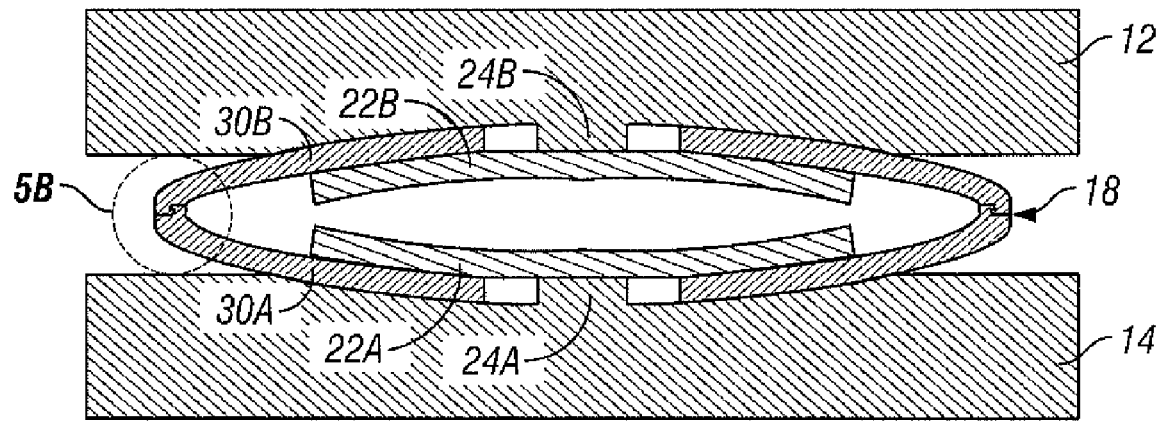
FIGS. 5A and 5B show a cross sectional view of a specific embodiment of the sliding capsule design of FIG. 2.
Figure 5B:
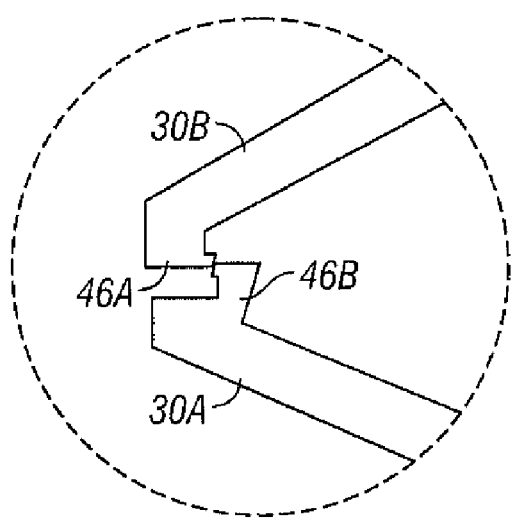

An alternative embodiment is illustrated in cross section in FIG. 5. This embodiment corresponds to the capsule design illustrated in general in FIG. 2. In this design, the retainer disks 22A and 22B and the inner sliding disks 30A and 30B are curved in the opposite contour from the embodiment of FIGS. 1 and 3-4. Thus, in the embodiment of FIG. 5, the concave sides of the retainer disks and sliding disks face each other, and the convex sides face corresponding concave surfaces of the endplates 12, 14. Operation of this embodiment is analogous to that described above, with the inner sliding disks 30A and 30B sliding along the endplate inner surfaces and between the retainer disks and the endplate surfaces during flexion, extension, and lateral bending of the spinal column.

One advantage of the design of FIG. 5 is that the clamp 40A, 40B of FIGS. 3 and 4 can be eliminated. This can be accomplished by including mating press-fit flanges 46A, 46B around the outer edges of the two sliding disks 30A, 30B. To assemble the device, each half is constructed comprising an endplate, a retainer disk, and a sliding inner disk. Then, the two halves are coupled with a snap fit that engages the flanges 46A, 46B and holds the two halves together.

All components of the device may be made of biocompatible metals and metal alloys such as stainless steel or titanium. In one embodiment, the sliding coefficient of friction between the disks and the endplate surfaces is reduced by coating the sliding surfaces with a low friction coating. One example of such a useful coating is known as Casidiam™ diamond-like carbon coating. This coating typically includes carbon, hydrogen, and possibly some additional dopant materials and is a mixture of tertagonal diamond type carbon crystal structure and trigonal graphitic carbon crystal structure. It is a commercially available coating and is used in a variety of industrial and medical applications requiring hardness, chemical inertness, biocomaptibility, and low friction.

The device may be installed in a variety of ways. The device may, for example, be installed in an anterior surgical procedure using installation and securement methods currently used for artificial disks of conventional design. For example, the endplates 12, 14 could include vertically extending central fins to engage the vertebral bodies on either side of the disk. This installation technique, however, has serious drawbacks. First, anterior installation is inherently risky due to the presence of the large blood vessels that run down the anterior of the spinal column. These vessels are especially vulnerable in the event the artificial disk needs to be removed, as revision surgeries must contend with scar tissue and adhesions that form in the surgical field and attach to these vessels. It is therefore desirable to provide an artificial disk design that is installed via a posterior or posterior-lateral approach. Although beneficial from a surgical point of view, the spinal cord, facets, lamina, and other bony structures in the posterior of the spine limit the available insertion space. This difficulty has limited the availability of posterior inserted artificial disks. To resolve this difficulty, and to increase the use of minimally invasive procedures, an especially advantageous embodiment has been designed in which the artificial disk is placed inside the disk space in several separate individual smaller pieces and is assembled within the disk space.

In one such embodiment, a pair of bone plates, each of which comes in two pieces, are installed and fixed to the upper and lower vertebral bodies. The bone plates include aligned channels into which a cassette comprising the central capsule 18 plus the two endplates 12, 14 is inserted. The artificial disk thus comes in a five-piece assembly that is inserted into the disk space one piece at a time, allowing for a smaller incision and surgical field and making posterior installation of an artificial disk a practical surgical alternative.

Figure 6:
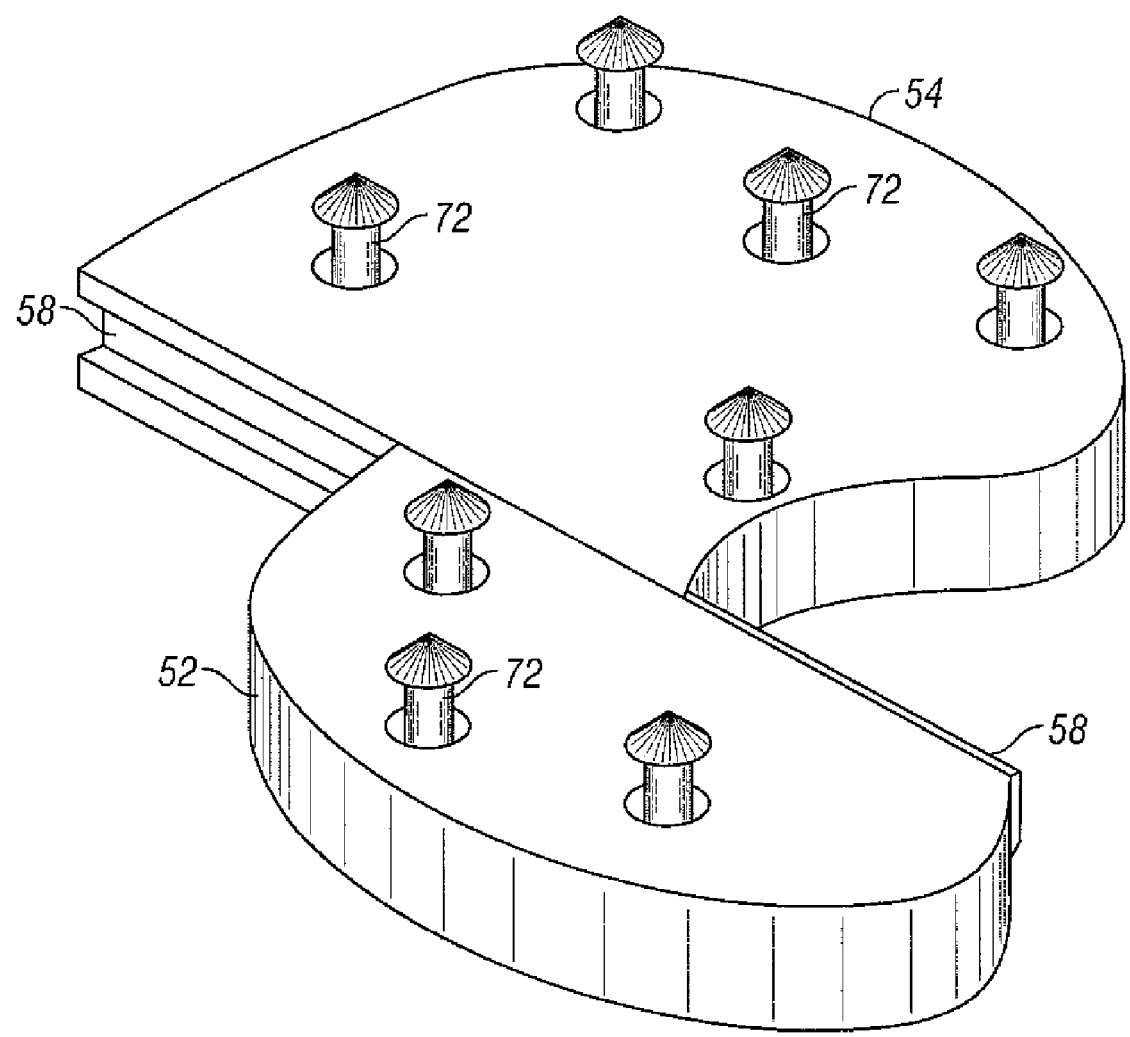
FIG. 6 is a perspective view of a multi-piece bone plate for coupling the sliding capsules to upper and lower vertebral bodies.
Figure 7A:
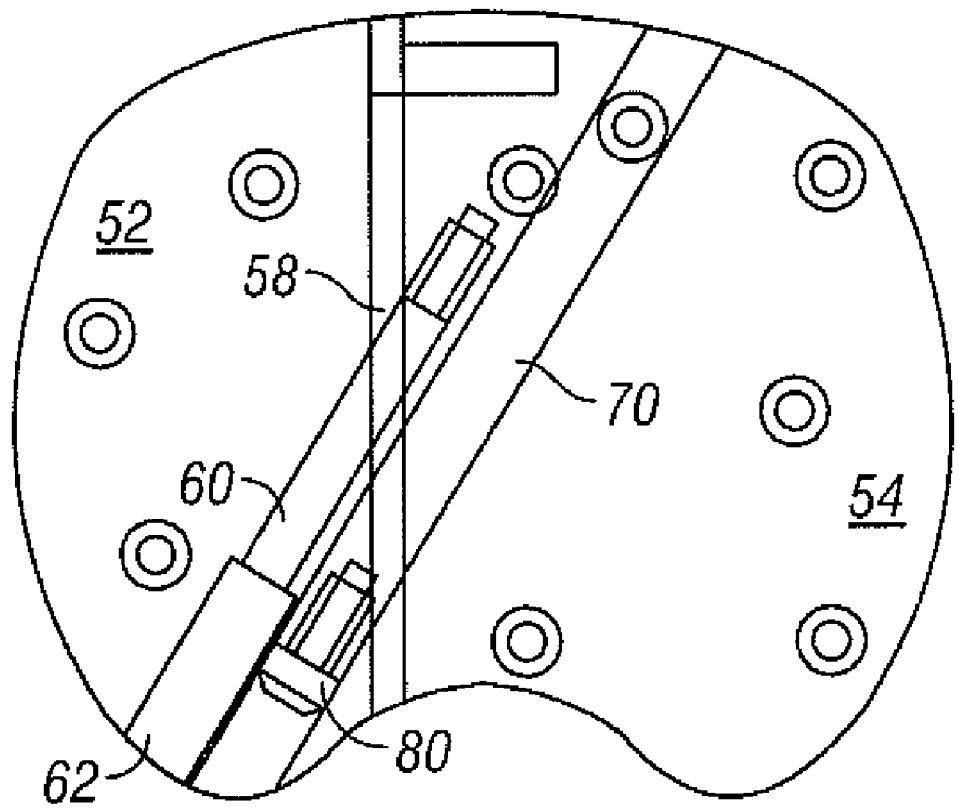
FIGS. 7A and 7B are top and side views of a specific embodiment of a bottom bone plate.
Figure 7B:
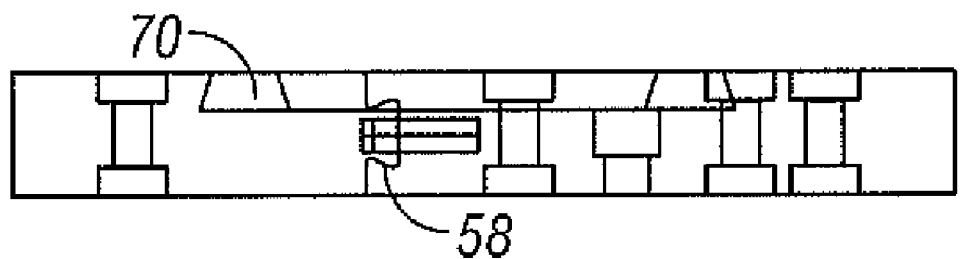
Figure 8A:
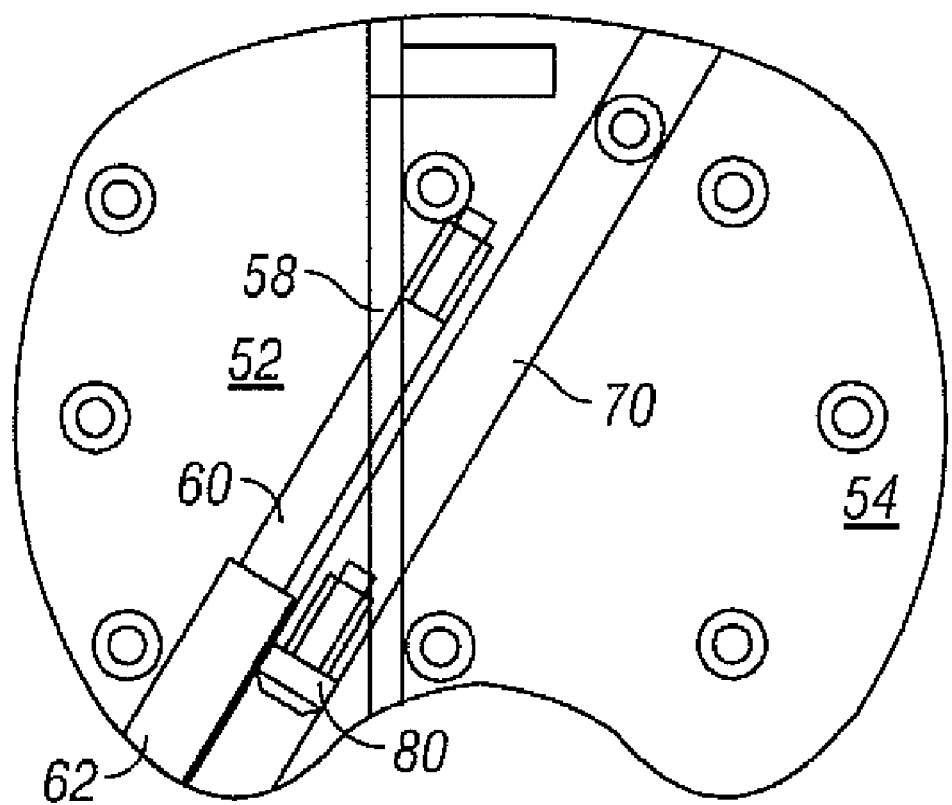
FIGS. 8A and 8B are top and side views of a specific embodiment of a top bone plate.
Figure 8B:
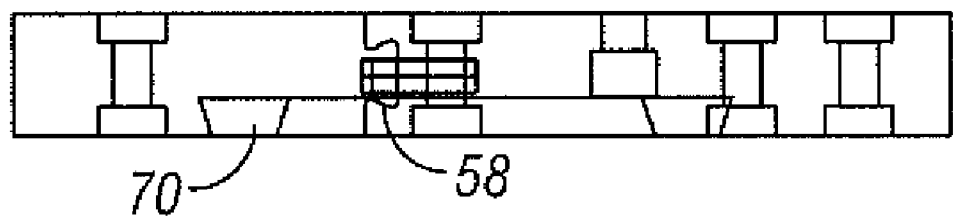

Bone plates which may be used in one such embodiment are illustrated in FIGS. 6 through 8. FIG. 6 is a general conceptual 3-D view from above an upper bone plate. FIGS. 7A-B and 8A-B show plan views and side views of upper and lower bone plates according to one embodiment of the invention.

In this embodiment, each bone plate includes a larger section 54 and a smaller section 52. The two sections are coupled together by a tongue and groove mating region 58. In the embodiment of FIG. 6, the larger section 54 includes a dovetail groove on a straight interior edge, and the smaller section includes a mating dovetail flange on an adjacent straight interior edge. The two pieces 52, 54 are further held together with a screw 60 (FIGS. 7 and 8) that is installed into a countersunk hole in the smaller section 52 and which terminates in a threaded hole in the larger section 54. When installed, this screw holds the two parts 52, 54 firmly together such that relative motion along the grooved mating region 58 is prevented after the pieces are installed.

The bone plates may also incorporate captured pins 72 that are deployed into the vertebral body after installation. A variety of pin deployment methods are known and could be used, including those described in U.S. Pat. Nos. 5,800,547; 5,123, 926; and 5,102,950, all three of which are hereby incorporated by reference in their entireties.

When mated as shown in FIGS. 7A and 8A, the two sections 52 and 54 create a dovetail channel 70 that extends diagonally on the surface of each bone plate. As described briefly above, the channels 70 accept mating dovetail flanges which extend from the outer surfaces of the endplates 12, 14 of FIGS. 1 to 3. In this way, the cassette comprising the end-plates and sliding capsule can itself be slid into position between the bone plates after installation of the bone plates.

In one embodiment, disk installation proceeds as follows. A lateral posterior hemilaminotomy insicion is made and the natural disk is resected in a conventional manner. For the bone plate design shown in FIGS. 6-8, this incision would be on the left of the spine. After removal of the natural disk, the larger of the two bone plate sections 52 for either the top or bottom vertebral body is inserted through the incision. This section of the bone plate is then pushed laterally over to the right side of the disk space into alignment with the right side of the vertebral body and such that the groove on its flat interior edge runs substantially straight from back to front. The captured pins 72 are now deployed. The most convenient method is typically the insertion of an expandable device that presses the pins into place in the facing bone tissue. After the larger section 54 is installed, the smaller section 52 is installed by sliding it straight into the left side of the disk space such that its dovetail flange is engaged with the dovetail groove in the first section 54 and such that the channel 70 is aligned across the entire bone plate. The pins of the second installed section 52 are then deployed in the same manner as the first. This same procedure is repeated to attach a bone plate to the other vertebral body. To ensure that the channels 70 in both bone plates are appropriately aligned along their length and with each other, it is possible to use a tool that can slide into both channels to test that they do not diverge in position or direction from back left to front right along the bone plate surfaces.

After the bone plates of FIGS. 7 and 8 are installed, the cassette comprising the endplates 12, 14, and central sliding capsule 18 is inserted by mating a dovetail flange on the outer surfaces of the endplates 12/14 (not shown in FIGS. 3 and 4) to the dovetail grooves 70 and sliding the cassette into position between the bone plates and approximately the center of the disk space. The cassette can be held in place with a set screw 80. A conceptual side view of an assembly is pictured in FIG. 9.

Figure 10:
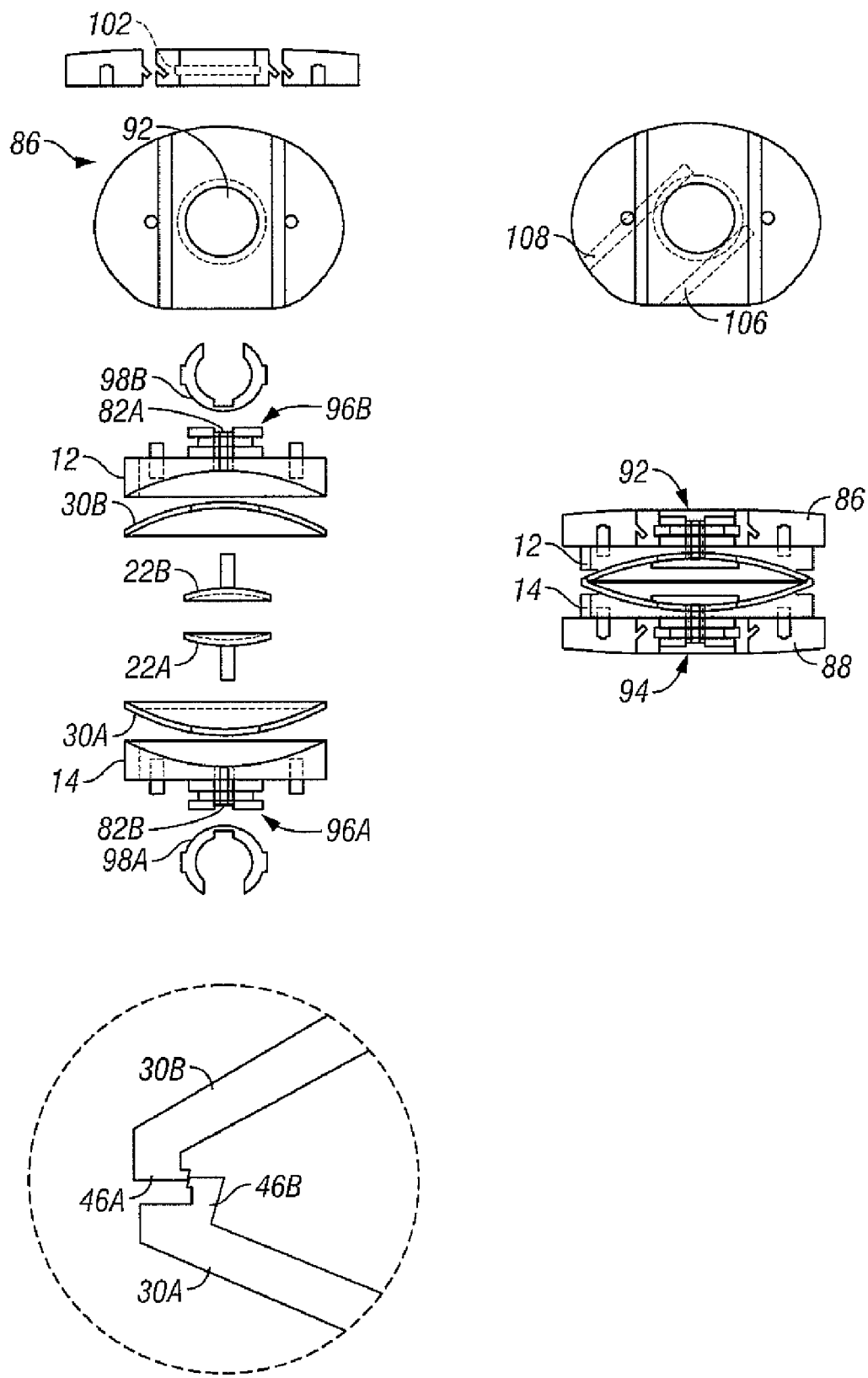
FIG. 10 illustrates an alternative artificial disk embodiment.
Figure 11E:
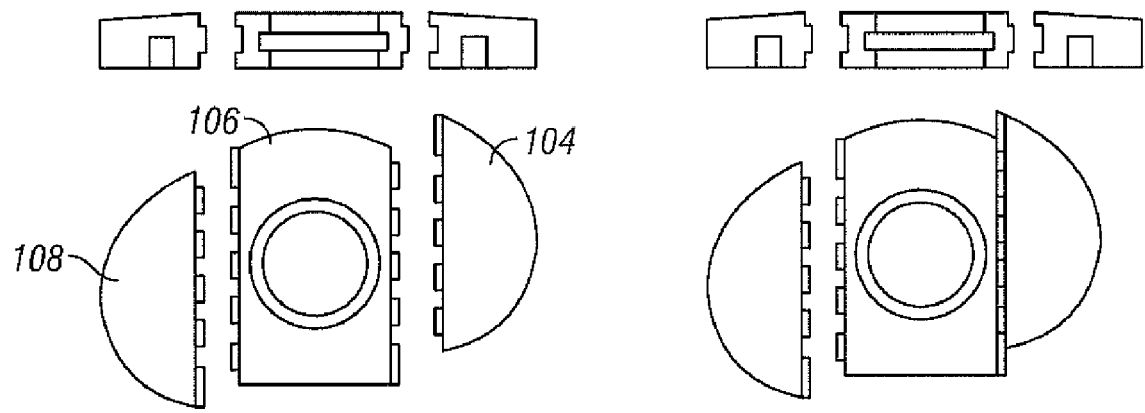
Figure 11E:
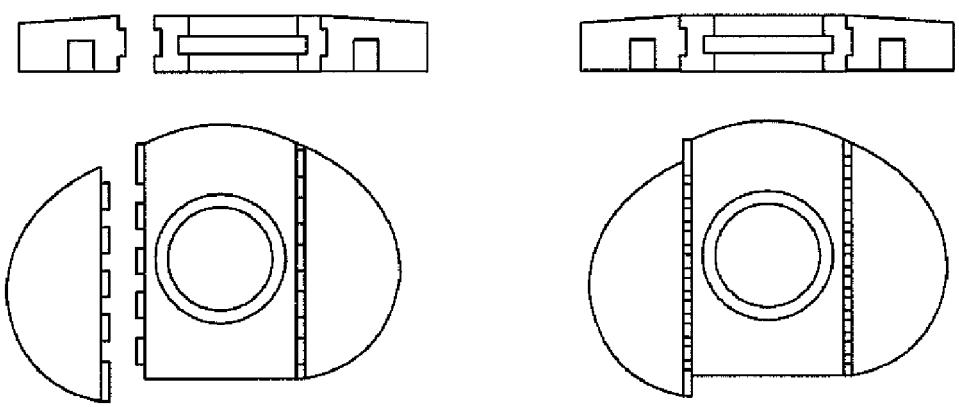
Figure 11E:
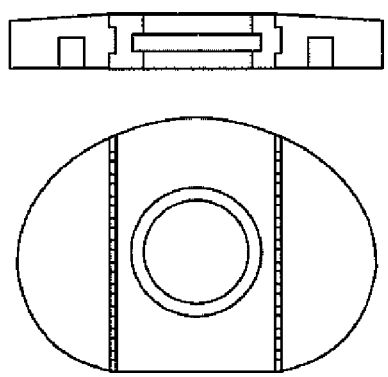
Figure 12A:
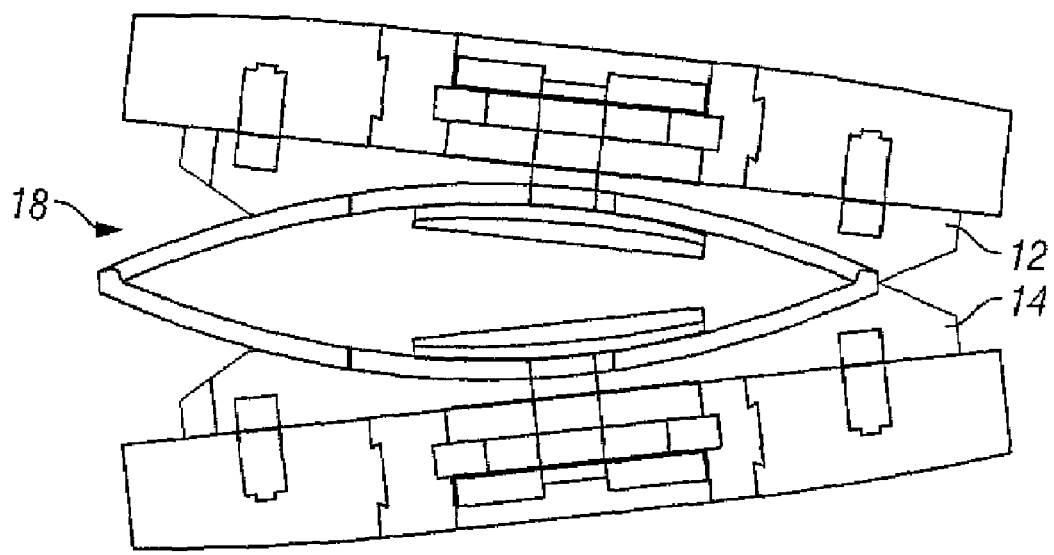
FIGS. 12A and 12B are side cutaway views of the artificial disk embodiment of FIG. 10.
Figure 12B:
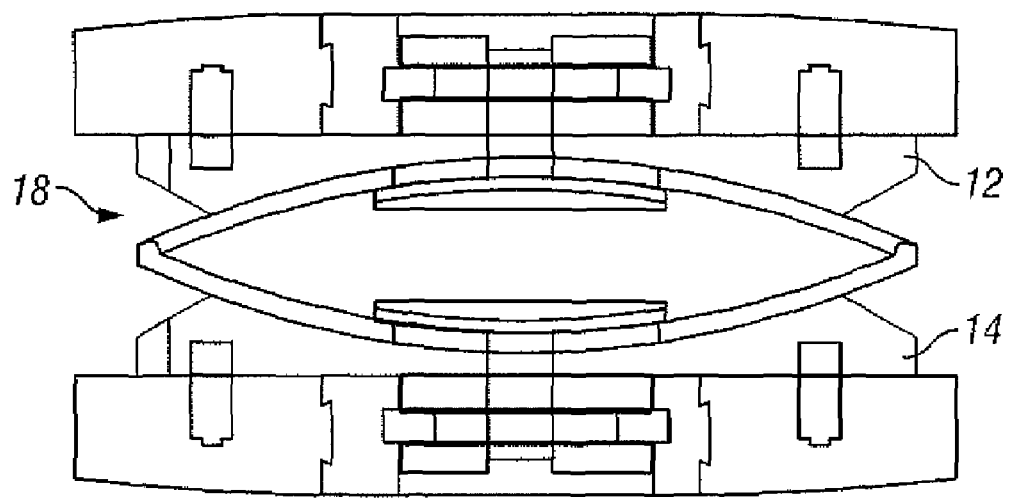

An embodiment having a central capsule similar to that described above with reference to FIGS. 2 and 5 is illustrated in FIGS. 10-12. As with the embodiment of FIG. 5, sliding disks 30A, 30B slide between the endplate inner surfaces and the bottom surfaces of inner retaining disks 22A, 22B. The retaining disks, in this embodiment, comprise threaded shafts that are screwed into threaded through holes 82A, 82B in the end plates 12, 14. After they are threaded down to the appropriate clearance, the bottom of the shafts are orbited in place to lock them tightly and prevent any rotation or movement out of position. In this embodiment, the endplates 12, 14 are captured in between the bone plates 86,88 through central orifices 92, 94. Grooved posts 96A, 96B extend from each endplate 14, 12 respectively. Captured in each grooved post is a snap ring. When the posts are engaged in the bone plates 86,88 ears on each snap ring engage an internal groove 102 in the orifice of each bone plate 86,88.

As shown in FIG. 11, the endplates may come in three parts instead of two as shown in FIGS. 6-8. The rightmost portion 104 may be installed first, followed by the central portion 106, and then the left-most portion 108. The portions are engaged by a series of mating dovetail tongue and groove segments. In the embodiment of FIG. 11, the central portion 106 has groove segments on the left, and tongue segments on the right. With this design, a tongue and groove mating along about half of the length of the bone plates can be made during installation with a sliding motion of only the length of a single dovetail segment. If desired, lips above and/or below the segments can be provided to discourage bone growth between the segments after installation.

FIG. 12 illustrates the embodiment of FIG. 10 after complete assembly. With this embodiment, the centerline of the device moves in accordance with the human body in relationship to the centerline, mimicking the response of a natural disk.

To install the device in the spinal column, the bone plates are installed as shown in FIG. 11. The bone plates may include deployable spikes or pins as described above, or they may have integral pre-deployed pins on their outer surfaces that are pressed into the vertebral bodies during installation.

The vertebra are then distracted to allow the central cassette comprising endplates 12, 14, central sliding capsule to be inserted between them. The vertebra are distracted to allow clearance for the posts 96A, 96B before they are set in the orifices 92, 94 in the bone plates. Once the posts are aligned with the orifices, the distraction is removed, and the posts drop into the orifices, engaging each snap ring 98A, 98B in its respective groove in the bone plate. The snap rings may be dimensioned to deform slightly during installation and snap into place, or a tool can be used to compress the rings slightly and allow the posts to engage the orifices. Toll access holes 106, 108 can be provided for this purpose, and to compress the rings for cassette removal, should removal be necessary.

The facets can also be addressed at the same time the artificial disk is being placed, and attention to the spinous process abutment can also be addressed at the time of surgery. In some surgical procedures, the posterior elements will also have an implant applied to the facets to improve on range of motion in flexion and extension without pain. These facet implants or articulations will facilitate the gliding mechanism that is well documented on scinradiography when the spine is taken through a range of motion in flexion, extension, lateral bend and torque. If the facet joint is not addressed, which is a significant stabilization unit of the motion segment, there may continue to be problems with back pain. At the time of our artificial disk implantation, the capsule of the facet joint may be removed, and a metal on metal artificial facet may be inserted to minimize pain and to preserve movement.

The facet arthroplasty will be an articulation with the inferolateral facet and superomedial facet. This arthroplasty will have a mechanism that will allow flexion, extension and lateral translation to occur. This arthroplasty may be accomplished by opening the facet joint and placing the implants on the articular cartilage (as illustrated in FIG. 2 for example). In may cases there may hypertrophy or arthrosis to these complexes, which may require a partial resection with a high speed burr or osteotome. Once the opening in the facet joint is achieved the arthroplasty can then be undertaken, and the implants are then attached to the inferior aspect of the ventral surface of the vertebra above and to the dorsal articulating surface of the vertebra below. With this facet arthroplasty done bilaterally, which can be achieved through minimally invasive technology, and the artificial disk in place, we have now addressed the three articulations, anterior, middle column and posterior.

The spinous processes can be partially resected to give space if there is abutment noted. A space may be created between the spinous processes to allow a placement of a shield with a metal on metal articulation at the spinal laminar junction of the vertebra above and below. This metal on metal articulation will give some partial support and also prevent the abutment of spinous processes which would restrict range of motion and could result in pain. This will not only give a partial ligamentous stability, but will also keep the spinous processes from abutting. As you can see, our artificial disk complex comprises both a posterior placement or lateral placement of the disk with supplementing the facet and possibly the spinous processes. Therefore, the entire complex anterior, middle and posterior column can be addressed to preserve circumferential stability to the motion segment. The artificial disk embodiments described herein do not preclude the device from being placed anteriorly, but it may often be preferable to perform one incision that can address both the posterior elements, as well as the interbody disk level with that one incision.

Figure 9:
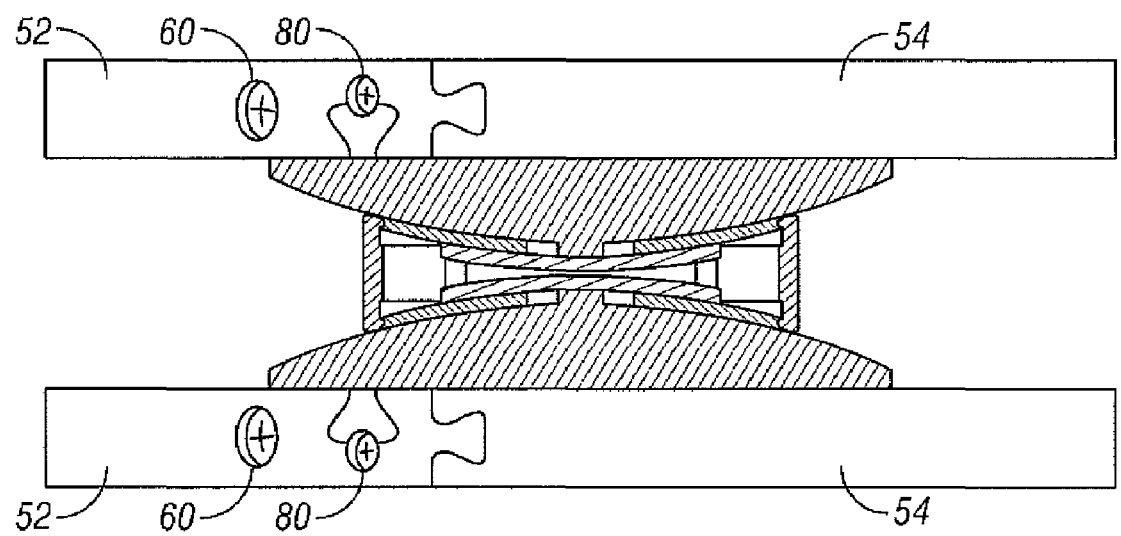
FIG. 9 is a side view of the capsule of FIG. 3 (in cross section) coupled to the top and bottom bone plates of FIGS. 7 and 8.

This modular design has a variety of advantages. One advantage already mentioned is that the design makes a posterior surgical approach practical. The bone plates for the vertebral bodies are inserted in multiple pieces. As shown in FIG. 9, the cassette itself can be made smaller than the bone plates, allowing insertion through the same small posterior lateral hemilaminotomy incision following the two-piece bone plates.

Another advantage to this design is that it allows the artificial disk to be easily replaced with a fusion cage if this becomes necessary. In such a revision surgery, the artificial disk cassette can be pulled out, and replaced with another cassette comprising a fusion cage filled with harvested bone. In some embodiments, the cassette could include an attachment point for a slap-hammer so that the cassette could be removed more easily. This process is much simpler and less traumatic than current artificial disk removal procedures. With conventional anterior installations, implant removal to perform a fusion often involves significant bone removal from the vertebral bodies to get the implant out.

The modular design described above can even be useful as a replacement for a removed disk as well. Because the bone plates are separate from the central cassette, the bone plates can be made in varying thicknesses, or two or more can be stacked, so that if bone removal from the vertebral bodies has significantly extended the height of the disk space, this can be compensated for by extended bone plate thickness. Thus, during revision surgeries, the bone plates can be exchanged for different versions having alternative thicknesses and sizes.

To further produce an easy and successful transition from artificial disk to fusion, the bone plates can be made fenestrated. In some embodiments it might be desirable to replace solid plates with fenestrated ones during the revision surgery to convert from an artificial disk to a fusion. As another alternative, fenestrated bone plates could be removably attached to solid covers that are left in place when used with an artificial disk installation but which are removed during a revision to a fusion.

What is claimed is:

1. An artificial spinal disk comprising:
   a first bone plate comprising a plurality of segments configured to attach to a first vertebral body;
   a second bone plate comprising a plurality of segments configured to attach to a second vertebral body;
   a central capsule comprising:
      a first central capsule plate configured to attach to said first bone plate and having an inwardly directed surface;
      a second central capsule plate configured to attach to the second bone plate and having an inwardly directed surface facing generally toward said inwardly directed surface of said first central capsule plate; and
      a pair of coupled sliding disks with outwardly directed opposed faces that slidably mate with respective ones of said inwardly directed surfaces of said first and second central capsule plates, wherein each of said sliding disks has an opening therethrough and is attached to a respective one of said central capsule plates with a retainer disk, said retainer disk being attached to a post coupled to said respective central capsule plate, said post extending through said opening, and said retainer disk having a surface larger than said opening in the sliding disk to capture said sliding disk between said retainer disk and said inwardly directed surface of said central capsule plate such that said sliding disk slides along and between spaced apart surfaces of said retainer disk and said central capsule plate.

2. The artificial spinal disk of claim 1, wherein at least one of said outwardly directed surfaces of said central capsule is convexly curved toward a mating inwardly directed surface of a central capsule plate.

3. The artificial spinal disk of claim 1, wherein the central capsule is configured to slide laterally within the disk space with one or more of flexion, extension, and lateral bending of the spine so as to shift an instantaneous center of rotation of the artificial disk.

4. The artificial disk of claim 1, wherein said first and second sliding disks are coupled along a circumferential edge thereof 5. A surgical kit for spinal surgery comprising:
   a first bone plate, wherein the first bone plate is configured for attachment to a first vertebral body;

a second bone plate, wherein the second bone plate is configured for attachment to a second vertebral body;

a central capsule, wherein the central capsule is configured to couple to said first bone plate and said second bone plate, wherein said central capsule comprises:

a first and second endplate each having a concave surface;

a first sliding disk and a second sliding disk configured to fit with the concave surfaces of said first endplate and said second endplate respectively, and wherein each of said sliding disks has an opening therethrough and is attached to a respective one of said endplates with a retainer disk attached to a post coupled to said respective endplate, said post extending through said opening, and wherein said retainer disk has a surface larger than said opening in the sliding disk to slidably capture said sliding disk between said retainer disk and said concave surface of said endplate such that said sliding disk slides along and between spaced apart surfaces of said retainer disk and said endplate;

wherein the first bone plate and the second bone plate attach to said central capsule via grooves on each of said first and second bone plates which slidably attach to tongues on each of said first and second endplates; and wherein said first bone plate, said second bone plate, and said central capsule are uncoupled from one another to allow for separate placement into the disk space during spine surgery.

6. The surgical kit of claim 5, wherein said first bone plate and said second bone plate comprise a plurality of uncoupled segments.

* * * * *